US010025002B2

(12) United States Patent
Price et al.

(10) Patent No.: US 10,025,002 B2
(45) Date of Patent: Jul. 17, 2018

(54) OPTICAL COMPUTING DEVICES COMPRISING BROADBAND ANGLE-SELECTIVE FILTERS

(71) Applicant: Halliburton Energy Services, Inc., Houston, TX (US)

(72) Inventors: James M. Price, Spring, TX (US); David L. Perkins, The Woodlands, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/306,868

(22) PCT Filed: Apr. 15, 2015

(86) PCT No.: PCT/US2015/025866
§ 371 (c)(1),
(2) Date: Oct. 26, 2016

(87) PCT Pub. No.: WO2016/167757
PCT Pub. Date: Oct. 20, 2016

(65) Prior Publication Data
US 2017/0052279 A1    Feb. 23, 2017

(51) Int. Cl.
*G01V 5/08* (2006.01)
*G01V 8/22* (2006.01)
(Continued)

(52) U.S. Cl.
CPC ............... *G01V 8/22* (2013.01); *E21B 49/08* (2013.01); *G01N 21/27* (2013.01); *G01N 21/85* (2013.01); *G01N 21/31* (2013.01)

(58) Field of Classification Search
CPC ...... H01L 31/0232; H01L 31/04; G02B 27/42
See application file for complete search history.

(56) References Cited

U.S. PATENT DOCUMENTS

| 6,198,531 B1 | 3/2001 | Myrick et al. |
| 6,529,276 B1 | 3/2003 | Myrick |

(Continued)

FOREIGN PATENT DOCUMENTS

| WO | 2015116153 A1 | 8/2015 |
| WO | 2015163853 A1 | 10/2015 |

OTHER PUBLICATIONS

Shen et al., "Optical Broadband Angular Selectivity," Jun. 8-13, 2014, CLEO Applications and Technology 2014, San Jose, California, USA, two pages.*

(Continued)

*Primary Examiner* — Kiho Kim
(74) *Attorney, Agent, or Firm* — McDermott Will & Emery LLP

(57) ABSTRACT

Optical computing devices including an electromagnetic radiation source to emit electromagnetic radiation into an optical train; an integrated computational element (ICE) located in the optical train before or after a sample located in the optical train to generate modified electromagnetic radiation in the optical train; a broadband angle-selective filter (BASF) located in the optical train to transmit the electromagnetic radiation and/or the modified electromagnetic radiation in the optical train at a target incident angle, thereby generating angle selected-modified electromagnetic radiation (ASMR), and to reflect one or more stray radiation reflections at angles that are not coincident with the target incident angle; and a detector to receive the ASMR and to generate an output signal corresponding to a characteristic of the sample.

18 Claims, 3 Drawing Sheets

(51) Int. Cl.
*G01N 21/27* (2006.01)
*G01N 21/85* (2006.01)
*E21B 49/08* (2006.01)
*G01N 21/31* (2006.01)

(56) References Cited

U.S. PATENT DOCUMENTS

| | | | |
|---|---|---|---|
| 7,123,844 B2 | 10/2006 | Myrick | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 8,049,881 B2 | 11/2011 | Myrick et al. | |
| 8,519,325 B1 | 8/2013 | Lu et al. | |
| 8,575,541 B1 | 11/2013 | Jamison et al. | |
| 8,575,584 B2 | 11/2013 | Jamison et al. | |
| 8,619,256 B1 | 12/2013 | Pelletier et al. | |
| 2009/0073433 A1 | 3/2009 | Myrick et al. | |
| 2009/0182693 A1 | 7/2009 | Fulton et al. | |
| 2009/0219538 A1 | 9/2009 | Myrick et al. | |
| 2009/0219539 A1 | 9/2009 | Myrick et al. | |
| 2010/0225911 A1* | 9/2010 | Cohen | G01J 3/02 356/326 |
| 2012/0037217 A1* | 2/2012 | Hamam | B82Y 20/00 136/253 |
| 2012/0236297 A1 | 9/2012 | Uematsu et al. | |
| 2012/0320578 A1 | 12/2012 | Flaming et al. | |
| 2013/0031964 A1 | 2/2013 | Tunheim et al. | |
| 2013/0031970 A1 | 2/2013 | Freese et al. | |
| 2013/0031971 A1 | 2/2013 | Freese et al. | |
| 2013/0031972 A1 | 2/2013 | Freese et al. | |
| 2013/0032333 A1 | 2/2013 | Freese et al. | |
| 2013/0032334 A1 | 2/2013 | Freese et al. | |
| 2013/0032338 A1 | 2/2013 | Kalia et al. | |
| 2013/0032339 A1 | 2/2013 | Kalia et al. | |
| 2013/0032340 A1 | 2/2013 | Freese et al. | |
| 2013/0032344 A1 | 2/2013 | Freese et al. | |
| 2013/0032345 A1 | 2/2013 | Freese et al. | |
| 2013/0032545 A1 | 2/2013 | Freese et al. | |
| 2013/0032736 A1 | 2/2013 | Tunheim et al. | |
| 2013/0033701 A1 | 2/2013 | Tunheim et al. | |
| 2013/0033702 A1 | 2/2013 | Tunheim et al. | |
| 2013/0034842 A1 | 2/2013 | Tunheim et al. | |
| 2013/0035262 A1 | 2/2013 | Freese et al. | |
| 2013/0284894 A1 | 10/2013 | Freese et al. | |
| 2013/0284895 A1 | 10/2013 | Freese et al. | |
| 2013/0284896 A1 | 10/2013 | Freese et al. | |
| 2013/0284897 A1 | 10/2013 | Freese et al. | |
| 2013/0284898 A1 | 10/2013 | Freese et al. | |
| 2013/0284899 A1 | 10/2013 | Freese et al. | |
| 2013/0284900 A1 | 10/2013 | Freese et al. | |
| 2013/0284901 A1 | 10/2013 | Freese et al. | |
| 2013/0284904 A1 | 10/2013 | Fresse et al. | |
| 2013/0286398 A1 | 10/2013 | Freese et al. | |
| 2013/0286399 A1 | 10/2013 | Freese et al. | |
| 2013/0287061 A1 | 10/2013 | Freese et al. | |
| 2013/0324819 A1 | 12/2013 | Colvin | |
| 2014/0061449 A1 | 3/2014 | Tunheim et al. | |
| 2014/0061513 A1 | 3/2014 | Tunheim et al. | |
| 2014/0067268 A1 | 3/2014 | Tunheim et al. | |
| 2014/0076549 A1 | 3/2014 | Pelletier et al. | |
| 2014/0076550 A1 | 3/2014 | Pelletier et al. | |
| 2014/0076551 A1 | 3/2014 | Pelletier et al. | |
| 2014/0078499 A1 | 3/2014 | Tunheim et al. | |
| 2014/0080172 A1 | 3/2014 | Tunheim et al. | |
| 2014/0080223 A1 | 3/2014 | Tunheim et al. | |
| 2014/0080224 A1 | 3/2014 | Tunheim et al. | |
| 2014/0081594 A1 | 3/2014 | Tunheim et al. | |
| 2014/0110105 A1 | 4/2014 | Jones et al. | |
| 2014/0116120 A1 | 5/2014 | Seckar | |
| 2014/0121970 A1 | 5/2014 | Ljungdahl | |
| 2014/0166361 A1 | 6/2014 | Jamison et al. | |
| 2014/0166871 A1 | 6/2014 | Jamison et al. | |
| 2014/0172177 A1 | 6/2014 | Jamison et al. | |
| 2014/0202689 A1 | 7/2014 | Walton et al. | |
| 2014/0231071 A1 | 8/2014 | Walton et al. | |
| 2015/0346084 A1 | 12/2015 | Russell et al. | |
| 2016/0091478 A1 | 3/2016 | Ceceil et al. | |
| 2016/0252652 A1* | 9/2016 | Shen | G02B 1/005 359/485.02 |

OTHER PUBLICATIONS

ISR/WO dated Jan. 25, 2016 for related PCT Application No. PCT/US2015/025866 filed Apr. 15, 2015.

Shen et al., Optical Broadband Angular Selectivity, Science, Mar. 28, 2014, 343(6178) 1499-1501.

B. T. Sullivan and J. A. Dobrowolski, "Implementation of a numerical needle method for thin-film design," Appl. Opt. 35, 5484-5492 (1996).

J. A. Dobrowolski and R. A. Kemp, "Refinement of optical multilayer systems with different optimization procedures," Appl. Opt. 29, 2876-2893 (1990).

Siegel et al., "Common Organic Contaminants in Cement and Bentonite Used for Water and Monitoring Well Construction," Chesapeake Energy, Jul. 10, 2013.

Sukhoivanov et al., Physics and Practical Modeling, ISMN 978-3-642-02645-4, Chapter 1, Introduction to Photonic Crystals (2009).

* cited by examiner

OPTICAL COMPUTING DEVICES COMPRISING BROADBAND ANGLE-SELECTIVE FILTERS

BACKGROUND

The embodiments herein generally relate to systems and methods of optical computing and, more specifically, to optical computing devices comprising broadband angle-selective filters.

Optical computing devices, also commonly referred to as opticoanalytical devices, may provide improved sensitivity and detection limits when integrated computational elements are used. Such integrated computational elements may provide a relatively low cost, rugged, and accurate system for monitoring petroleum quality for the purpose of optimizing decision making at a well site and efficient management of hydrocarbon production. In some applications, the integrated computational elements may be useful in improving detection limits when determining a particular characteristic of a sample, such as a substance, compound, or material present in a wellbore, or other technology fields including, but not limited to, the food and drug industry, industrial applications, mining industries, or any field where it may be advantageous to determine in real-time a characteristic of a substance, compound, or material.

Stray light reflections in optical computing devices, however, may interfere with the measurement of the sample when the reflections are not from the sample itself but from some other source. Such stray light reflections may be a significant fraction of the total light (e.g., electromagnetic radiation) detected in the optical computing device. If not effectively reduced or otherwise prevented, the stray light may vary the resulting sample signal, resulting in substantially reduced accuracy, precision, sensitivity, and limit of detection. For example, such variations include, but are not limited to, large bias voltages observed in a detector, lower resolution in spatial images, detector saturation effects, combinations thereof, or the like. Traditionally, such stray light reflections are controlled or minimized using imaging lenses, anti-reflective coatings, physical apertures, and the like. However, such techniques may not adequately remove stray light reflections, resulting in improved, but still non-optimal signals related to the sample of interest

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
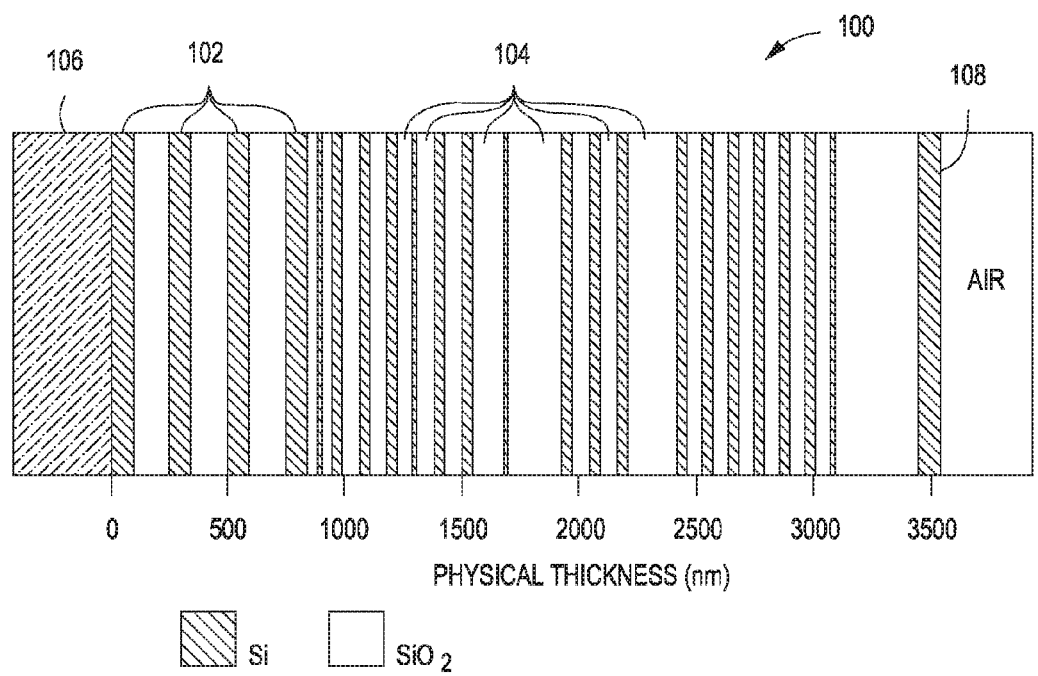
FIG. 1 illustrates an exemplary integrated computation element, according to one or more embodiments described herein.

The embodiments herein generally relate to systems and methods of optical computing and, more specifically, to optical computing devices comprising broadband angle-selective filters.

The exemplary systems and methods described herein employ various configurations of optical computing devices, also commonly referred to as "opticoanalytical devices," employing broadband angle-selective filters (BASF) for the rapid analysis of a characteristic of a sample of interest, such as a sample in a flow path, a static sample, a sample on a conveyor belt, and the like. The disclosed systems and methods may be suitable for use in the oil and gas industry since the described optical computing devices provide a cost-effective, rugged, and accurate means for identifying one or more characteristics of a sample of interest in order to facilitate oil and gas production and/or safety of oil and gas wells. For example, the optical computing devices described herein may identify a characteristic of a sample in a flow path, such as a wellbore. Such characteristics may allow monitoring of petroleum quality for the purpose of optimizing decision making at a well site and efficient management of hydrocarbon production. In some applications, the optical computing devices disclosed herein may be useful in improving detection limits when determining a particular characteristic of a substance, compound, or material present in a wellbore by reducing or eliminating stray light reflections. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a sample of interest, including flowing samples. As used herein, the term "flowing" refers to circulation or movement of a fluid sample with reference to the optical computing devices disclosed herein.

One or more illustrative embodiments incorporating the disclosure herein are presented below. Not all features of an actual implementation are described or shown in this application for the sake of clarity. It is to be understood that in the development of an actual embodiment incorporating the present disclosure, numerous implementation-specific decisions must be made to achieve the developer's goals, such as compliance with system-related, business-related, government-related and other constraints, which may vary by implementation and from time to time. While a developer's efforts might be complex and time-consuming, such efforts would be, nevertheless, a routine undertaking for one having ordinary skill in the art and the benefit of this disclosure.

It should be noted that when "about" is provided herein at the beginning of a numerical list, the term modifies each number of the numerical list. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquid and/or gases. Illustrative gases that can be considered fluids according to the present embodiments include, for example, air, nitrogen, carbon dioxide, argon, helium, hydrogen disulfide, mercaptan, thiophene, methane, ethane, butane, and other hydrocarbon gases, and/or the like.

As used herein, the term "characteristic" refers to a chemical or physical property of a substance. A characteristic of a substance may include a quantitative value of one or more chemical components therein. Such chemical components may be referred to as "analytes." Illustrative characteristics of a substance that can be monitored with the optical computing devices disclosed herein may include, for example, chemical composition (identity and concentration, in total or of individual components), impurity content, pH, viscosity, density, ionic strength, total dissolved solids, salt content, porosity, opacity, bacteria content, combinations thereof, and the like.

As used herein, the term "electromagnetic radiation" refers to infrared radiation, near-infrared radiation, visible light, ultraviolet light, vacuum ultraviolet light, X-ray radiation, gamma ray radiation, and any combination thereof.

As used herein, the term "optical computing device" refers to an optical device that is configured to receive an input of electromagnetic radiation from a substance or sample of the substance (collectively referred to as "sample") and produce an output of electromagnetic radiation from a processing element. The processing element may be, for example, an integrated computational element ("ICE"). The electromagnetic radiation emanating from the processing element is changed in some way so as to be readable by a detector, such that an output signal of the detector may be correlated to at least one characteristic of the sample. The output of electromagnetic radiation from the processing element can be reflected electromagnetic radiation, transmitted electromagnetic radiation, and/or dispersed electromagnetic radiation. As will be appreciated, whether reflected or transmitted electromagnetic radiation is analyzed by the detector will be a matter of routine experimental design. In addition, emission and/or scattering of the substance, for example via fluorescence, luminescence, radiating and re-radiating, Raman scattering, and/or Raleigh scattering can also be monitored by the optical computing devices.

As used herein, the term "sample," or variations thereof, refers to at least a portion of a substance of interest to be tested or otherwise evaluated using the optical computing devices described herein. The sample includes the characteristic of interest, as defined above, and may be any fluid, as defined herein, or otherwise any solid substance or material such as, but not limited to, rock formations, concrete, other solid surfaces, etc.

As used herein, the term "optically-interact" or variations thereof refers to the reflection, transmission, scattering, diffraction, radiating, re-radiating, or absorption of electromagnetic radiation either on, through, or from one or more processing elements, such as integrated computational elements. Accordingly, optically-interacted light refers to light that has been reflected, transmitted, scattered, diffracted, or absorbed by, emitted, radiated or re-radiated, for example, using the integrated computational elements, but may also apply to interaction with a sample substance.

Unlike conventional spectroscopic instruments, which measure and produce an electromagnetic spectrum of a sample needing further interpretation to obtain a result, the ultimate output of optical computing devices described herein is a real number that can be correlated in some manner with a characteristic of a sample of interest. In addition, significant benefits may be realized by including in the optical computing devices one or more broadband angle-selective filters that reduce or eliminate stray light reflections that may interfere with the output signal related to a characteristic of a sample. As used herein, a "broadband angle-selective filter" (or "BASF") refers to a filter that screens broadband light with respect to an angle of incidence. As used herein, the term "angle of incidence" refers to the angle that an incident ray of electromagnetic radiation makes normal to a surface.

In addition, significant benefits may be realized by combining the outputs from two or more integrated computational elements and/or two or more BASFs within an optical computing device with one another, as will be further described below, when analyzing a sample. Specifically, in some instances, significantly increased detection accuracy may be realized. Any of the methods described herein may be carried out by combining the outputs of two or more integrated computational elements and/or two or more BASFs with one another. The integrated computational elements and/or BASFs whose outputs are being combined may be associated or disassociated with a characteristic of interest, display a positive or negative response when analyzing the characteristic of interest, or any combination thereof.

As alluded to above, the operational simplicity of optical computing devices makes them rugged and well suited for field or process environments, including deployment within a subterranean formation. For example, the optical computing devices described herein may analyze fluids commonly encountered in the oil and gas industry, including while deployed within a subterranean formation.

A significant and distinct advantage of the optical computing devices disclosed herein is that they can be configured to specifically detect and/or measure a characteristic of a sample, thereby allowing qualitative and/or quantitative analyses of the characteristic without having to undertake a time-consuming sample processing procedure, or without having to record and process the sample's electromagnetic spectrum. With rapid analyses capabilities on hand, the exemplary systems and methods described herein may be able to determine the percentage of a characteristic of a sample so that an operator may determine whether the characteristic is within a particular acceptable limit range. If the characteristic of the sample is outside of the acceptable limit range (typically too high), then corrective measures may be taken. The use of the optical computational devices described herein to detect a characteristic of a sample may further be beneficial to allow for the collection and archival of information relating to such samples for particular operations, in conjunction with operational information, to optimize subsequent operations, and the like.

In some embodiments, the present disclosure provides an optical computing device comprising an electromagnetic radiation source that emits electromagnetic radiation into an optical train. As used herein, the term "optical train" refers to the path that electromagnetic radiation traverses originating at a source and terminating at a detector. Within the optical train, a sample, an ICE, and a BASF are positioned in any configuration. That is, the sample may come before or after the ICE, the ICE may come before or after the BASF, and the BASF may come before or after the sample. Moreover, more than ICE and/or more than one BASF may be in the optical train, without departing from the scope of the present disclosure.

The exemplary systems and methods described herein include at least one optical computing device configured to measure at least one characteristic of a sample, such as in a flow path which may be in a subterranean formation (e.g., a wellbore). In some embodiments, the optical computing devices suitable for use in the exemplary systems and methods described herein may be mobile or portable.

In accordance with the embodiments described herein, an optical computing device may include an electromagnetic radiation source, at least one processing element (e.g., an ICE), at least one BASF, and at least one detector arranged to receive optically interacted light after it has interacted with the at least one ICE, the at least one BASF, and a sample, in any combination. However, in at least one embodiment, the electromagnetic radiation source may be omitted and instead the electromagnetic radiation may be derived from the sample itself. In some embodiments, the exemplary optical computing devices may be specifically configured for detecting, analyzing, and quantitatively measuring a particular characteristic of a sample, such as a concentration of a component of the sample or other characteristics discussed in greater detail below. In other embodiments, the optical computing devices may be general purpose optical devices, with post-acquisition processing (e.g., through computer means) being used to specifically detect the characteristic of the sample.

The presently described optical computing devices combine the advantage of the power, precision, and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics of a sample. In some embodiments, the detected output can be converted into a current or voltage that is distinctive of the magnitude of the characteristic of the sample.

The optical computing devices of the present disclosure operate by discriminating between optical (or voltage) signals related to a characteristic of a sample and interfering signals (e.g., stray light or "ghost" signals). Such stray light (also referred to as "stray light reflections" and "stray radiation reflections" herein) relates to an optical signal that is not related to the sample of interest, and that may have a tendency to vary the desired signal conveyed through the optical train and corresponding to the sample or characteristic thereof. If not effectively reduced or otherwise prevented, the stray light may serve to adversely vary the detected electromagnetic radiation, resulting in substantially reduced accuracy, precision, sensitivity, and limit of detection. Previous means of reducing stray light relied on physical masking techniques, apertures, and shields, for example. However, the embodiments herein synergistically combine one or integrated computational element(s) and broad-band selectivity filter(s) to reduce or eliminate stray light and increase the sensitivity and output signal of the optical computing devices comprising them (e.g., reduce the signal-to-noise ratio), as compared to previously used means.

The optical computing devices can be configured to detect not only the composition and concentrations of a sample, but they can also be configured to determine physical properties and other characteristics of the sample as well, based on their analysis of the electromagnetic radiation received from the optical train comprising the sample. For example, the optical computing devices can be configured to determine the concentration of the sample and correlate the determined concentration to a characteristic of the sample by using suitable processing means. As will be appreciated, the optical computing devices may be configured to detect as many characteristics as desired for a given sample. All that is required to accomplish the monitoring of multiple characteristics of interest is the incorporation of suitable processing and detection means within the optical computing device for each characteristic of interest (e.g., concentration of an analyte, and the like). In some embodiments, the properties of the sample may be determined using a combination of characteristics of interest (e.g., a linear, non-linear, logarithmic, and/or exponential combination). Accordingly, the more characteristics that are detected and analyzed using the optical computing devices, the more accurately the properties of the sample will be determined. For example, properties of a sample that may be determined using optical computing devices described herein may include, but are not limited to, the absolute concentration of an analyte, the relative ratios of two or more analytes, the presence or absence of an analyte, and the like, and any combination thereof.

The optical computing devices described herein utilize electromagnetic radiation to perform calculations, as opposed to the hardwired circuits of conventional electronic processors. When electromagnetic radiation interacts with a sample, unique physical and chemical information about the sample may be encoded in the electromagnetic radiation that is reflected from, transmitted through, or radiated in an optical train comprising the sample. The optical computing devices described herein are capable of extracting the information of the spectral fingerprint of multiple characteristics of a sample, and converting that information into a detectable output regarding the overall properties of the monitored material of interest. That is, through suitable configurations of the optical computing devices, electromagnetic radiation associated with characteristics of interest can be separated from electromagnetic radiation associated with all other components of the material of interest in order to estimate the properties of the monitored substance (e.g., a contaminant) in real-time or near real-time, particularly by synergistic operation of the one or more ICEs and one or more BASFs comprising the optical computing devices.

The processing elements used in the exemplary optical computing devices described herein may be characterized as integrated computational elements (ICE). Each ICE is capable of distinguishing electromagnetic radiation that has optically interacted with a sample in an optical train from other electromagnetic radiation. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and SiO$_2$ (quartz), respectively. In general, these layers 102, 104 consist of materials whose index of refraction is high and low, respectively. Other examples might include niobia and niobium, germanium and germania, MgF, SiO$_x$, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and SiO$_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 may contain a corresponding vessel (not shown), which houses the gases or liquids. Exemplary variations of the ICE 100 may also include holographic optical elements, gratings, piezoelectric, light pipe, digital light pipe (DLP), molecular factor devices, variable optical attenuators, and/or acousto-optic elements, for example, that can create transmission, reflection, and/or absorptive properties of a material of interest or contaminant.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the integrated output light intensity of the ICE 100 is related to the characteristic of interest.

The BASF of the present disclosure may be used at any location in the optical train, described in more detail below, to reflect stray electromagnetic radiation, thereby enhancing the signal in the optical train relating to the sample or characteristic of interest of the sample that is received by a detector. Specifically, the BASF transmits electromagnetic radiation and reflects one or more stray light reflections at angles that are not coincident with a target incident angle. Additionally, because the refractive index of many types of samples may not be highly sensitive to wavelength, the target incident angle may be the same for a broad band of frequencies using the same BASF. The BASF reflects all or substantially all electromagnetic radiation propagating at angles that are not coincident with the target incident angle. As used herein, the term "substantially" means largely, but not necessarily wholly.

Any BASF may be used in the optical train in accordance with the methods of the present disclosure. In some embodiments, the ability of a BASF to reflect stray light and transmit signals at a target angle of incidence may depend largely on the existence of optical band gaps in the BASF that prevent light propagation at particular frequencies and transmit those at an incident angle, and the ability of photonic heterostructures to broaden such band gaps. As used herein, the term "band gap," and grammatically variants thereof, refers to ranges of photon frequencies where no photons can be transmitted through a material. As used herein, the term "photonic heterostructures" (or simply "heterostructures") refers to a stacking of photonic materials (e.g., photonic crystals) having different optical refractive indices. In some embodiments, the heterostructures described herein may be formed using quarter-wave stacks having varying refractive indices, each one quarter of an optical wavelength in thickness.

The "refractive index" of a material (e.g., a sample of interest) of an optical medium is a dimensionless number that describes how much electromagnetic radiation is bent, or refracted, as it propagates through a material. The refractive index (n) of a material is determined by Equation 1:

$$n = \sqrt{\varepsilon_r \mu_r}$$

Equation 1, where $\varepsilon_r$ is the material's relative permittivity, and $\mu_r$ is the material's relative permeability. A materials relative permittivity and relative permeability are frequency, and thus wavelength, dependent. Typically, for most naturally occurring materials, the relative permeability of a material is substantially equal to one (the integer 1) at optical frequencies (although not always) and, accordingly, the variable refractive indices of the photonic material (e.g., photonic crystal) in the heterostructures described herein may be based substantially, or wholly, on the material's relative permittivity.

Figure 2:
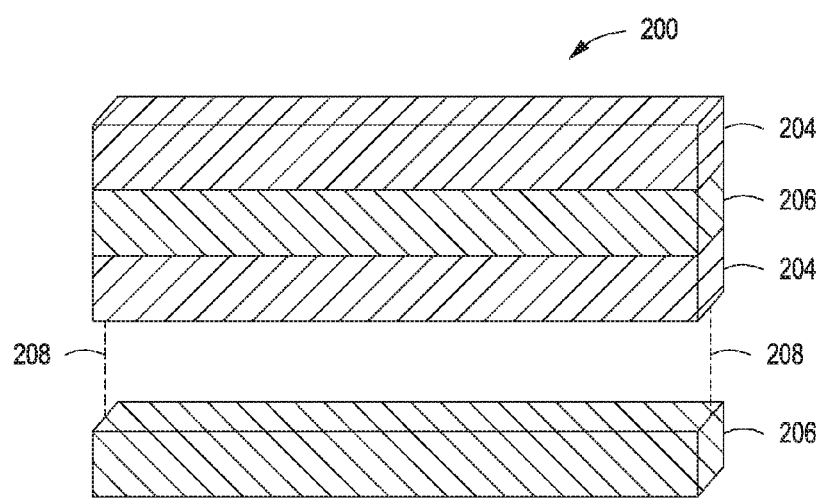
FIG. 2 illustrates a representative photonic heterostructure for use as a broadband angle-selective filter, according to one or more embodiments described herein.

Referring now to FIG. 2, illustrated is a representative photonic heterostructure 200 that may be used to form the BASFs of the present disclosure. The heterostructure 200 is formed from alternating layers of a high-index photonic material 204 and a low-index photonic material 206. As depicted by the dashed lines 208, the number of layers of high-index photonic material 204 and low-index photonic material 206 may vary depending on the design of the heterostructure 200. For example, the layers of the heterostructure 200 may comprise greater than about 5 bilayers, where a bilayer includes one high-index material 204 layer and one low-index material 206 layer. That is, the number of bilayers is not limited according to the methods of the present disclosure. In some embodiments, the number of bilayers in the quarter-wave stack 202 may be between a lower limit of about 5 bilayers, 10 bilayers, 20 bilayers, 30 bilayers, 40 bilayers, 50 bilayers, 60 bilayers, 70 bilayers, 80 bilayers, 90 bilayers, 100 bilayers, 110 bilayers, 120 bilayers, 130 bilayers, 140 bilayers, 150 bilayers, 160 bilayers, 170 bilayers, 180 bilayers, 190 bilayers, 200 bilayers, 210 bilayers, 220 bilayers, 230 bilayers, 240 bilayers, and 250 bilayers to an upper limit of about 500 bilayers, 490 bilayers, 480 bilayers, 470 bilayers, 460 bilayers, 450 bilayers, 440 bilayers, 430 bilayers, 420 bilayers, 410 bilayers, 400 bilayers, 390 bilayers, 380 bilayers, 370 bilayers, 360 bilayers, 350 bilayers, 340 bilayers, 330 bilayers, 320 bilayers, 310 bilayers, 300 bilayers, 290 bilayers, 280 bilayers, 270 bilayers, 260 bilayers, and 250 bilayers, encompassing any value and subset therebetween, even or odd. In some embodiments, each of the layers or bilayers may additionally comprise bilayers to further refine the band gaps desired for a particular BASF comprising the heterostructure 200.

As an increasing number of high-index photonic material 204 and low-index photonic material 206 bilayers are added, the transmission of certain incident angles of electromagnetic radiation decreases, thus increasing reflection of these incident angles. As depicted, the heterostructure 200 comprises alternating layers of high-index photonic material 204 and low-index photonic material 206 bilayers; however, in other embodiments, the heterostructure 200 may have photonic material layers (or bilayers, or layers comprising one or more bilayers) that represent a geometric series of refractive indices, such that the refractive indices of the layers increase or decrease geometrically, thereby also modifying the band gap for particular wavelengths of electromagnetic radiation.

As depicted, the heterostructure 200 includes 1:1 stacks (i.e., bilayers) having equal thickness, such as equal optical thickness (e.g., one quarter of an optical wavelength in thickness). However, higher-order stacking may also be suitable for use as the BASF of the present disclosure. For example, 2:1 or 3:1 stacking may be suitable of high-index photonic material 204:low-index photonic material 206, or of low-index photonic material 206:high-index photonic material 204. Other higher-order stacking may also be employed, without departing from the scope of the present disclosure. Moreover, the double or triple stacking of one type of photonic material may be effectively a single layer with an increased thickness. In these higher-order stacks, the ratio between the optical thickness of high-index photonic material and low-index photonic material may be adjusted in integer multiples, such as by reducing the thickness of the high-index photonic material while preserving the desired spectral band gaps.

In some embodiments, the size, thickness, or shape of two adjacent photonic materials in a heterostructure forming a BASF according to the present disclosure may be varied to achieve a desired band gap. For example (not shown), a second layer A may be arranged such that it is of a smaller size than a first and third layer B that surround layer A. The second layer A may have a photonic band gap that lies within the photonic band gap of the first and third layer B. Accordingly, electromagnetic radiation having a wavelength outside of the band gap of layer A but inside the band gap of layers B will be reflected by layers B and thus retained within layer A.

In some embodiments, the material forming the layers of the heterostructure 200 for forming the BASF may be any photonic crystal material including isotropic and anisotropic material, which may be alternated or otherwise arranged relative to each other in the layers forming the heterostructure 200. The photonic crystal layers may include, but are not limited to, a silicon-based compound (e.g., silicon dioxide, silicon, and the like), a tantalum-based compound (e.g., tantalum pentoxide), a Group III-V semiconductor compound (e.g., gallium arsenide, indium gallium arsenide, indium phosphide, and the like), a Group IVB metal compound (e.g., titanium oxide, hafnium oxide, zirconium oxide, and the like), a dielectric, and any combination thereof.

Figure 3A:
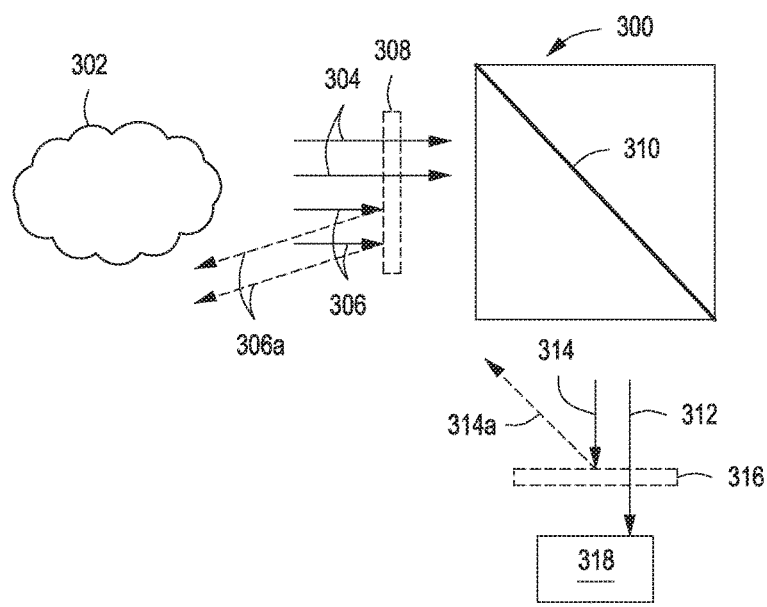
FIGS. 3A,B illustrate an optical computing device comprising a broadband angle-selective filter, according to one or more embodiments described herein.

Referring now to FIG. 3A, illustrated is a block diagram that non-mechanistically illustrates how an optical computing device 300 is able to distinguish electromagnetic radiation related to a characteristic of interest in a sample from other electromagnetic radiation, and how a BASF is able to distinguish electromagnetic radiation at a target incident angle from electromagnetic radiation that is not coincident with the target incident angle. As shown in FIG. 3A, after being illuminated with electromagnetic radiation, a sample 302 produces an output of electromagnetic radiation (e.g., sample-interacted light), some of which is electromagnetic radiation 304 corresponding to the characteristic of interest and characterized by a target incident angle, and some of which is background electromagnetic radiation 306 that may correspond to other characteristics of the sample 302 or other background electromagnetic radiation.

The sample-interacted light 304 and 306 may, in some embodiments, encounter a first BASF 308 (shown in phantom). The first BASF 308 may permit the sample-interacted light 304 corresponding to the characteristic of interest and at the target incident angle to transmit therethrough while reflecting the light 306 that is not coincident with the target incident angle, thereby forming reflected light 306a and directing it away from the optical computing device 300. Accordingly, the first BASF 308 may be employed in the optical computing device 300 in order to restrict the optical wavelengths and/or bandwidths of the system that are not coincident with the target incident angle, thereby eliminating unwanted electromagnetic radiation existing in wavelength regions that have no importance.

Figure 3B:
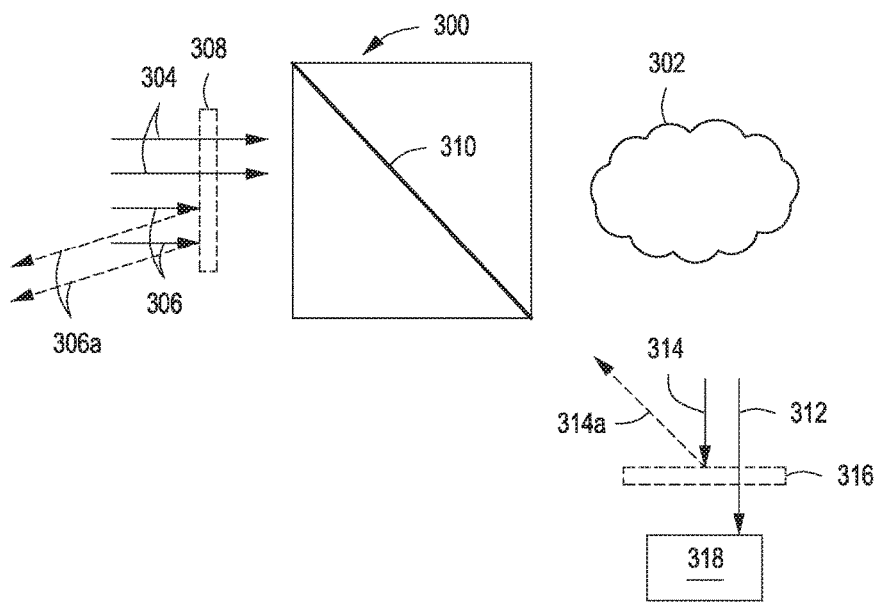

The beams of electromagnetic radiation 304 at the target incident angle when the first BASF 308 is employed impinge upon the optical computing device 300, which contains an exemplary ICE 310 therein. In the illustrated embodiment, the ICE 310 may be configured to process the sample-interacted light 304 and produce modified electromagnetic radiation 312 and 314. Modified electromagnetic radiation 312 corresponds to a target incident angle and modified electromagnetic radiation 314 corresponds to electromagnetic radiation (or simply "light" as used herein) that is not coincident with the target incident angle. In some embodiments, the target incident angle from the sample-interacted light 304 and the modified electromagnetic radiation 312 may be the same or different, without departing from the scope of the present disclosure. As used herein, the term "modified electromagnetic radiation" refers to electromagnetic radiation that has optically interacted with both a sample and an ICE in any order. For example, as shown in FIG. 3B and with continued reference to FIG. 3A, in some instances, optical computing device 301 may be configured such that the ICE 310 may be located before the sample 302 in an optical train, wherein electromagnetic radiation 304 first optically interacts with the ICE 310 to generate optically interacted radiation (e.g., ICE-interacted light) in an optical train, some of which is electromagnetic radiation 304 corresponding to the characteristic of interest and characterized by a target incident angle, and some of which is background electromagnetic radiation 306 that may correspond to other characteristics of the sample 302 or other background electromagnetic radiation. Then the optically interacted radiation optically interacts with the sample 302 to generate the modified electromagnetic radiation 312, 314 in the optical train. One or more BASFs (two shown) 308, 316 may additionally be positioned in the optical train to reflect light 306a, 314a at various points along the optical train. The modified electromagnetic radiation 312 may be conveyed to detector 318. In other embodiments, as is shown in FIG. 3A, the ICE 310 is located in the optical train after the sample 302, wherein the electromagnetic radiation 304 first optically interacts with the sample 302 to generate optically interacted radiation (e.g., sample-interacted light), and then the optically interacted radiation optically interacts with the ICE 310 to generate the modified electromagnetic radiation 312, 314 in the optical train. That is, the order of the sample 302 relative to the ICE 310 in the optical train is not limiting and does not interfere with the ability of the optical computing device 300 to detect a characteristic of interest of the sample 302.

As shown in FIG. 3A, in some embodiments, a second BASF 316 may be positioned in the optical train after the ICE 310 to transmit the modified electromagnetic radiation 312 that is at the target incident angle and to reflect the modified electromagnetic radiation 314 that is not coincident with the target incident angle, thereby forming reflected light 314a and directing it away from a detector 318. The first BASF 308 and second BASF 316 may be substantially or wholly similar (e.g., of the same material, layer size, tuned to the same target incident angle, and the like) or may be substantially different, without departing from the scope of the present disclosure. The type of BASF selected may depend on the target incident angle desired at any particular location in the optical train, which may itself depend on the sample 302 type, the characteristic of interest of the sample 302, the order of contact of electromagnetic radiation with the various components of the optical computing device 300, and the like. Moreover, the first BASF 308 or the second BASF 316 may each be used in the optical train alone or in combination with one another. Additionally, other BASFs (e.g., 308, 316) may be located in the optical train at any location, such as to fine-tune the transmission of the target incident angle and reflect stray light that is not coincident with the target incident angle. For example, a BASF may be located in the optical train between the electromagnetic radiation source and the sample, between the sample and the ICE, between the ICE and the detector, and any combination thereof.

The modified electromagnetic radiation 312 may be conveyed to the detector 318 for analysis and quantification. In some embodiments, the detector 318 may be configured to produce an output signal in the form of a current or voltage that corresponds to a particular characteristic of the sample 302. In at least one embodiment, the signal produced by the detector 318 and the characteristic of the sample 302 (e.g., concentration of an analyte of the sample 302) may be directly proportional. In other embodiments, the relationship may be a polynomial function, an exponential function, and/or a logarithmic function. The reflected stray light 306a, 314a, which may be related to other characteristics of the sample 302 or non-sample 302 related light may be directed away from the detector 318. In alternative configurations (not shown), the ICE 310 and/or BASFs 308, 316 may be configured such that the reflected optically interacted light 306a, 314a may be related to one characteristic of the sample 302, and the transmitted optically interacted and/or modified radiation 304, 312 may be related to another characteristic of the sample 302, without departing from the scope of the present disclosure, and the reflected optically interacted light 306a, 314a may be conveyed to a second detector (not shown) for analysis and quantification.

In some embodiments, the reflected optically interacted light 306a, 314a may be related to characteristics of the sample 302 that are not of interest or, in some instances, may be related to radiating deviations including, for example, intensity fluctuations in the electromagnetic radiation, interferent fluctuations (e.g., dust or other interferents passing in front of an electromagnetic radiation source), coatings on windows included with the optical computing device 300 (e.g., sample windows), combinations thereof, or the like.

The characteristic(s) of interest being analyzed using the optical computing device 300 may be further processed and/or analyzed computationally to provide additional characterization information about the sample 302, or an analyte thereof. In some embodiments, the identification and concentration of one or more analytes of a sample 302 may be used to predict certain physical characteristics of the sample 202, or analyte thereof. For example, the amount of the sample 202 may be evaluated to determine, for example, whether it is present within acceptable limits. Accordingly, where one or more optical computing devices 300 is used according to the methods herein to detect a characteristic of interest of a sample 302, different acceptable limit ranges may apply to the one or more characteristics.

In some embodiments, the magnitude of the characteristic of interest determined using the optical computing device 300 may be fed into an algorithm operating under computer control. The algorithm may be configured to determine whether the sample 302 or characteristic of interest of the sample 302 is in programmed acceptable limits, which may be narrowed depending on a particular operation. In some embodiments, the algorithm can produce an output that is readable by an operator who can manually take appropriate action, if needed, based upon the reported output. In some embodiments, the algorithm may direct the operator as to how to take a corrective action (e.g., how to bring the amount of the sample 302 or characteristic of interest of the sample 302 within acceptable limits). In other embodiments, the algorithm can take proactive process control (e.g., halt operations, alter a composition comprising the sample 302 or characteristic of interest of the sample 302, and the like). It is to be recognized that the algorithm (e.g., an artificial neural network) can be trained using samples of predetermined characteristics of interest, and thereby generating a virtual library. As the virtual library available to the artificial neural network becomes larger, the neural network can become more capable of accurately predicting the sample 302 or characteristic of interest of the sample 302. Furthermore, with sufficient training, the artificial neural network can more accurately predict the sample 302 or characteristic of interest of the sample 302, even in the presence of unknown analytes.

In some embodiments, the data collected using the optical computing devices 300 may be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system may also allow remote monitoring to take place. Automated control with a long-range communication system can further facilitate the performance of remote job operations. In particular, an artificial neural network can be used in some embodiments to facilitate the performance of remote job operations. That is, remote job operations may be conducted automatically in some embodiments. In other embodiments, however, remote job operations can occur under direct operator control, where the operator is not at the job site (e.g., via wireless technology).

Figure 4:
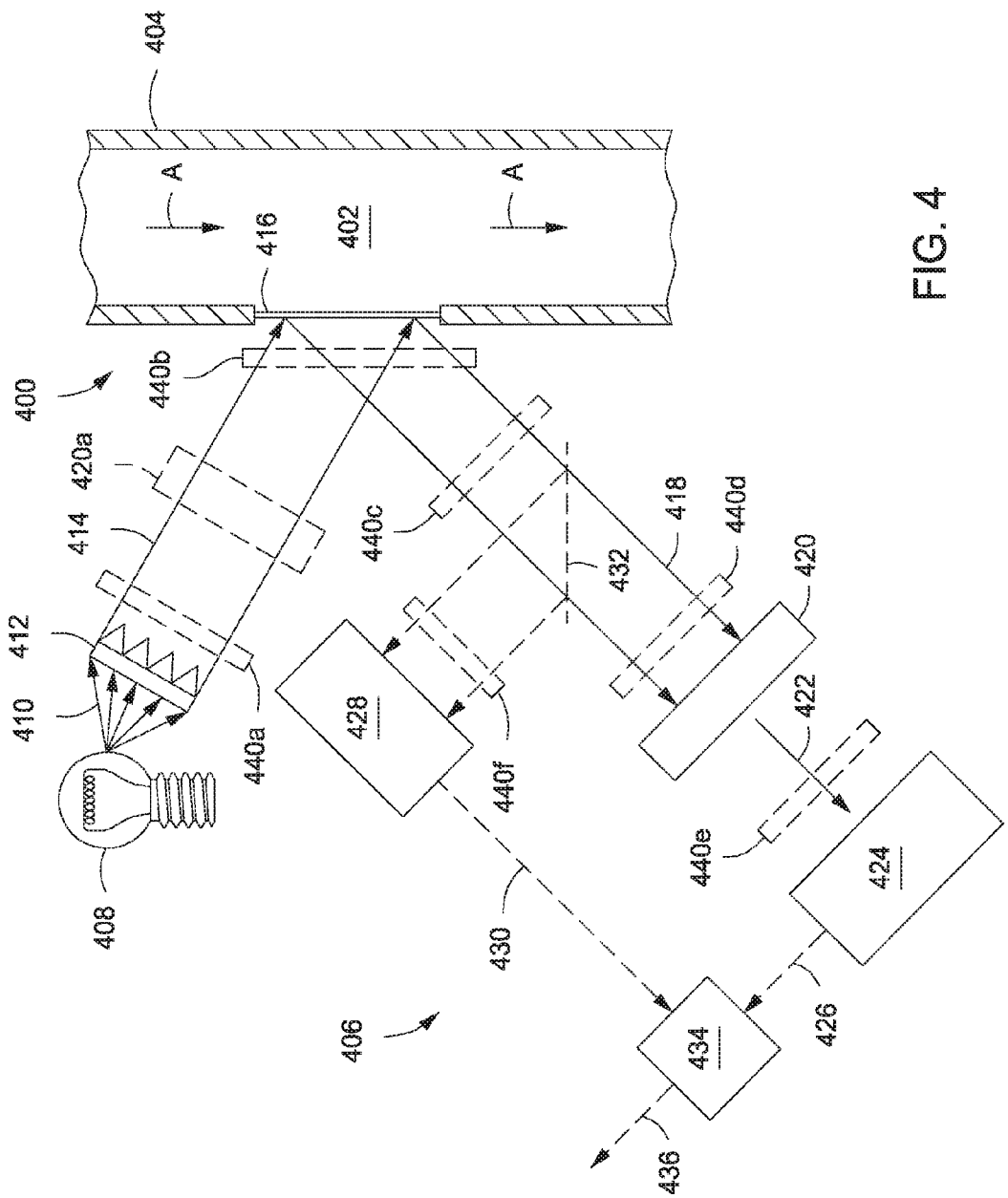
FIG. 4 illustrates an exemplary system for detecting a characteristic of a sample using an optical computing device comprising a broadband angle-selective filter, according to one or more embodiments.

Referring now to FIG. 4, illustrated is an exemplary system 400 for monitoring or determining a particular characteristic of a sample 402, according to one or more embodiments. In the illustrated embodiment, the sample 402 may be within a flow path 404, although the sample 402 need not be housed within a flow path 404 to comport with the embodiments described herein. The flow path 404 may be, for example, may be a portion of a sample chamber in a formation tester, or a portion of a wellbore, and the like. The sample 402 may be flowing or otherwise moving in the flow path 404 may be flowing in the general direction indicated by the arrows A (i.e., upstream to downstream). It will be appreciated, however, that the flow path 404 may be in any direction, including a circular direction, without departing from the scope of the present disclosure.

The system 400 may include at least one optical computing device 406, which may be similar in some respects to the optical computing device 300 of FIGS. 3A,B. While not shown, the device 406 may be housed within a casing or housing configured to substantially protect the internal components of the device 406 from damage or contamination from the external environment. The housing may operate to mechanically couple or otherwise place in communication the device 406 to the flow path 404 with, for example, mechanical fasteners, brazing or welding techniques, adhesives, magnets, other fastening devices, combinations thereof, or the like.

As described in greater detail below, the optical computing device 406 may be useful in determining a particular characteristic of a sample 402, such as one within the flow path 404. For example, the characteristic of the sample 402 may be the concentration of an analyte present within the sample 402. In some embodiments, the device 406 may include an electromagnetic radiation source 408 configured to emit or otherwise generate electromagnetic radiation 410. The electromagnetic radiation source 408 may be any device capable of emitting or generating electromagnetic radiation, as defined herein. For example, the electromagnetic radiation source 408 may be a light bulb, a light emitting device (LED), a laser, a blackbody, a photonic crystal, an X-Ray source, a gamma ray source, combinations thereof, or the like. In some embodiments, a lens 412 may be configured to collect or otherwise receive the electromagnetic radiation 410 and direct a beam 414 of electromagnetic radiation 410 toward the sample 402 in an optical train. The lens 412 may be any type of optical device configured to transmit or otherwise convey the electromagnetic radiation 410 as desired. For example, the lens 412 may be a normal lens, a Fresnel lens, a diffractive optical element, a holographic graphical element, a mirror (e.g., a focusing mirror), a type of collimator, or any other electromagnetic radiation transmitting device known to those skilled in the art. In other embodiments, the lens 412 may be omitted from the device 406 and the electromagnetic radiation 410 may instead be conveyed toward the sample 402 directly from the electromagnetic radiation source 408 in the optical train.

In one or more embodiments, the device 406 may also include a sampling window 416 arranged adjacent to or otherwise in contact with the sample 402 for detection purposes. The sampling window 416 may be composed from a variety of transparent, rigid or semi-rigid materials that are configured to allow transmission of the electromagnetic radiation 410 therethrough. For example, the sampling window 416 may be composed of, but is not limited to, glasses, plastics, semi-conductors, crystalline materials, polycrystalline materials, hot or cold-pressed powders, combinations thereof, or the like. Although a sample window 416 is depicted as part of the system 400 in FIG. 4, it will be appreciated that a sample window 416 may be omitted from the system 400 and the electromagnetic radiation 410 may optically interact with a sample 402 directly, without first passing through a sample window 416, without departing from the scope of the present disclosure.

As shown, after passing through the sampling window 416, the electromagnetic radiation 410 impinges upon and optically interacts with sample 402 in the flow path 404. As a result, optically interacted radiation 418 is generated by and reflected from the sample 402. Those skilled in the art, however, will readily recognize that alternative variations of the device 406 may allow the optically interacted radiation 418 to be generated by being transmitted, scattered, diffracted, absorbed, emitted, or re-radiated by and/or from the sample 402, or one or more analytes of the sample 402, without departing from the scope of the present disclosure.

The optically interacted radiation 418 generated by the interaction with the sample 402 may be directed to or otherwise received by an ICE 420 arranged within the device 406. The ICE 420 may be a spectral component substantially similar to the ICE 100 described above with reference to FIG. 1. Accordingly, in operation the ICE 420 may be configured to receive the optically interacted radiation 418 and produce modified electromagnetic radiation 422 corresponding to a particular characteristic of interest of the sample 402.

It should be noted, as previously discussed, that while FIG. 4 depicts the ICE 420 as receiving optically interacted radiation 418 from the sample 402, the ICE 420 may be arranged at any point along the optical train of the device 406, without departing from the scope of the disclosure. For example, in one or more embodiments, the ICE 420a (shown in phantom) may be arranged within the optical train prior to the sample 402 and the device 406 and equally obtain substantially the same results. Accordingly, the modified electromagnetic radiation 422 may be generated by optically interacting with at least one ICE and the sample 402 in any order, without departing from the scope of the present disclosure. In other embodiments, the sampling window 416 may serve a dual purpose as both a transmission window and an ICE (i.e., a spectral component). In yet other embodiments, the ICE 420 may generate the modified electromagnetic radiation 322 through reflection, instead of transmission therethrough.

Moreover, while only one ICE 420 is shown in the device 406, embodiments are contemplated herein which include the use of at least two ICE components in the device 406 configured to cooperatively determine the characteristic of interest in the sample 402. For example, two or more ICE components may be arranged in series or parallel within the device 406 at any point along the optical train and configured to receive the electromagnetic radiation 410 or optically interacted radiation 418 to enhance sensitivities and detector limits of the device 406. In other embodiments, two or more ICE components may be arranged on a movable assembly, such as a rotating disc or an oscillating linear array, which moves such that the individual ICE components are able to be exposed to or otherwise optically interact with electromagnetic radiation 410 for a distinct brief period of time. The two or more ICE components in any of these embodiments may be configured to be either associated or disassociated with the characteristic of interest in the sample 402. In other embodiments, the two or more ICE components may be configured to be positively or negatively correlated with the characteristic of interest.

In some embodiments, it may be desirable to monitor more than one characteristic of interest at a time using the device 406. In such embodiments, various configurations for multiple ICE components may be used, where each ICE component is configured to detect a particular and/or distinct characteristic of interest corresponding, for example, to a characteristic of the sample 402. In some embodiments, the characteristic of interest may be analyzed sequentially using multiple ICE components that in which a single beam of optically interacted radiation 418 is reflected from or transmitted through the sample 402. In some embodiments, multiple ICE 320 components may be arranged on a rotating disc, where the individual ICE components are only exposed to the beam of optically interacted radiation 418 for a short time. Advantages of this approach may include the ability to analyze multiple characteristics of interest of a sample 402 (or multiple types of samples 402) using a single device 406 and the opportunity to assay additional characteristics simply by adding additional ICE components corresponding to those additional characteristics or corresponding to different types of samples 402. Again, it should be noted, that the one or more ICE components may be located before, after, or before and after (i.e., where multiple ICE components are used) the sample 402, without departing from the scope of the present disclosure.

In other embodiments, multiple devices 406 may be placed at a single location along the flow path 404, where each device 406 contains a unique ICE that is configured to detect a particular characteristic of interest of the sample 402. In such embodiments, a beam splitter can divert a portion of the optically interacted radiation 418 being reflected by, emitted from, or transmitted through the sample 402 and into each device 406. As will be described in further detail below, a BASF according to the embodiments described herein may also be used as a beam splitter to achieve this purpose. Each device 406, in turn, can be coupled to a corresponding detector or detector array that is configured to detect and analyze an output of electromagnetic radiation from the respective device 406. Parallel configurations of optical computing devices 406 may be particularly beneficial for applications that require low power inputs and/or no moving parts.

The modified electromagnetic radiation 422 generated by the ICE 420 may subsequently be conveyed to a detector 424 for quantification of the signal. The detector 424 may be any device capable of detecting electromagnetic radiation, and may be generally characterized as an optical transducer. In some embodiments, the detector 424 may be, but is not limited to, a thermal detector such as a thermopile or photoacoustic detector, a semiconductor detector, a piezo-electric detector, a charge coupled device (CCD) detector, a video or array detector, a split detector, a quad detector, a photon detector (such as a photomultiplier tube), photo-diodes, combinations thereof, or the like, or other detectors known to those skilled in the art.

In some embodiments, the detector 424 may be configured to produce an output signal 426 in real-time or near real-time in the form of a voltage (or current) that corresponds to the particular characteristic of interest of the sample 402. The voltage returned by the detector 424 is essentially the dot product of the optical interaction of the modified electromagnetic radiation 422 with respect to the ICE 420 as a function of the characteristic of interest. As such, the output signal 426 produced by the detector 424 and the characteristic of interest may have a relationship that is directly proportional or may correspond to a polynomial function, an exponential function, a logarithmic function, a combination thereof, or the like.

In some embodiments, the device 406 may include a second detector 428, which may be similar to the first detector 424 in that it may be any device capable of detecting electromagnetic radiation. The second detector 428 may be used to detect radiating deviations stemming from the electromagnetic radiation source 408. Undesirable variations may occur in the intensity of the electromagnetic radiation 410 due to a wide variety of reasons and potentially causing various negative effects on the output of the device 406. These negative effects may be particularly detrimental for measurements taken over a period of time. In some embodiments, the variations may occur as a result of a build-up of film or material on the sampling window 416, which may have the effect of reducing the amount and quality of light ultimately reaching the first detector 424. Without proper compensation, such radiation deviations may result in false readings and the output signal 426 would no longer be primarily or accurately related to the characteristic of interest.

To compensate for these variations in light intensity, the second detector 428 may be configured to generate a compensating signal 430 generally indicative of the radiation deviations of the electromagnetic radiation source 408, and thereby normalize the output signal 426 generated by the first detector 424. As illustrated, the second detector 428 may be configured to receive a portion of the optically interacted radiation 418 via a beam splitter 432 in order to detect these variations. In other embodiments, however, the second detector 428 may be arranged to receive electromagnetic radiation from any portion of the optical train in the device 406 in order to detect the variations in source intensity, without departing from the scope of the disclosure.

In some applications, the output signal 426 and the compensating signal 430 may be conveyed to or otherwise received by a signal processor 434 communicably coupled to both the detectors 424, 428. The signal processor 434 may be a computer including a non-transitory machine-readable medium, and may be configured to computationally combine the compensating signal 430 with the output signal 426 in order to normalize the output signal 426 in view of any light source intensity variations detected by the second detector 428 and produce a resulting output signal 436. In some embodiments, computationally combining the output and compensating signals 426, 430 may entail computing a ratio of the two signals 426, 430. For example, the concentration or magnitude of each characteristic of interest determined using the optical computing device 406 may be fed into an algorithm run by the signal processor 434.

In real-time or near real-time, the signal processor 434 may be configured to provide the resulting output signal 436 corresponding to a characteristic of interest in the sample 402. The resulting output signal 436 may be readable by an operator who can consider the results and make proper adjustments or take appropriate action, if needed, based upon output signal related to the sample 402 (e.g., a concentration of the sample 402 or a concentration of a characteristic of the sample 402). In some embodiments, the resulting signal output 436 may be conveyed, either wired or wirelessly, to an operator for consideration. In other embodiments, the resulting output signal 436 of the characteristic of interest may be recognized by the signal processor 434 as being within or without an acceptable limit range for a particular operation and may alert the operator of an out of range reading so appropriate corrective action may be taken, or otherwise autonomously undertake the appropriate corrective action such that the resulting output signal 436 returns to a value within the predetermined or preprogrammed range of suitable operation.

The potential for stray radiation is not limited to any particular location within the optical train and may occur at any point in the optical train, thereby resulting in a potential reduction in the sensitivity of the device 406 to detect a characteristic of the sample 402, as previously discussed. For example, the sample window 416 may have one or more surfaces that generate at least one or more stray radiation reflections. Accordingly, regardless of the particular embodiment arrangement selected for the device 406 as described herein, one or more BASFs may be placed within any portion of the optical train of the device 406 to reflect stray light away from the optical train that are not coincident with a particular target incidence angle (including a broad band of angles, where appropriate) and transmit electromagnetic radiation that is coincident with the target incidence angle. For example, as shown in phantom in FIG. 4, the BASF may be located at one or more locations in the optical train between the electromagnetic radiation source 408 and the sample 402. For example, BASF 440*a* may be located between the electromagnetic radiation source 408 and the sample 402 near the electromagnetic radiation source 408 (e.g., just after the optional lens 412). In other embodiments, BASF 440*b* may be located between the electromagnetic radiation source 408 and the sample 402 near the sample 402 (e.g., near the sampling window 416). The BASFs of the present disclosure may additionally be located between the sample 402 and the ICE 420, such as at a location after the sampling window 416 (BASF 440*c*) or just prior to the ICE 420 (BASF 440*d*). In some embodiments, one or more BASF may be located between the ICE 420 and the detector 424 (BASF 440*e*).

In some embodiments, one or more BASFs may be located before or after the optional beam splitter 432 (e.g., BASF 440*c*, 440*d*), or the beam splitter 432 itself may be a BASF according to the methods of the present disclosure, such that the BASF beam splitter 432 is designed to transmit certain target incident angles and reflect others that are not coincident with a target incident angle, as previously described. One or more BASFs may also be located in the optical path after the beam splitter 432 and before the second detector 428, without departing from the scope of the present disclosure.

In each instance that a BASF is positioned in the optical train of the device 406, it may serve to transmit or reflect certain electromagnetic radiation with certain angles of incidence. That is, a characteristic of interest of a sample 402 or a particular ICE 420 may transmit or reflect light at a certain angle of incidence and the BASF may be designed as discussed previously, to transmit or reflect that angle of incidence which conversely reflecting or transmitting, respectfully, angles of incidence that are not coincident with the target angle. In each instance, the selection and design of the BASF may also take into account whether the electromagnetic radiation first reacts with the ICE 420 or the sample 402, has reacted with neither the sample 402 nor the ICE 420, has reacted with both the ICE 420 and the sample 402, and the like, depending on its location in the optical train. In such a manner, only or substantially only the electromagnetic radiation 410 of interest remains in the optical train or is otherwise controlled to remain in the optical train such that it can be taken into account in determining the output signal 422, 430.

In some embodiments, the BASF of the present disclosure may be a stand-alone filter. As used herein, the term "stand-alone filter," and grammatical variants thereof, refers to a broadband angle-selective filter as described herein that is not integral to any component of the optical computing devices described herein. When the BASF is a stand-alone filter, as described previously, it may be located at any location in the optical train including, but not limited to, between the electromagnetic radiation source and the sample, between the sample and the ICE, between the ICE and the detector, and any combination thereof. It may then interact with one or more of the electromagnetic radiation 410, the optically interacted radiation 418 (or optically interacted radiation that has interacted with an ICE and not yet the sample), the modified electromagnetic radiation 422 (that has interacted with at least one ICE and the sample in any order), and any combination thereof. After the electromagnetic radiation 410, the optically interacted radiation 418, and/or the modified electromagnetic radiation 422 optically interacts with the BASF, it may generate angle-selected modified electromagnetic radiation (ASMR) that is received by the detector 424 (and/or 428), which may then generate output signals corresponding to a characteristic of the sample 402.

As described herein, the BASF 440*a-f* may additionally be a multi-layer film stack that is deposited onto a component of the device 406 as a film. Such multi-layer film stack BASFs may be deposited onto a component including, but not limited to, the ICE 420, the detector 424, 428, the sampling window 416, and any combination thereof, provided that it is in the optical train. Standard thin film deposition methods may be utilized for depositing the multi-stack film layer onto one or more components of the device 406, without departing from the scope of the present disclosure. In some embodiments, the deposition may be achieved by fabricating the BASF from an optical substrate, which then may operate as the ICE 420. In other embodiments, the multi-layer film stack may be deposited onto one or more components of the device 406 using reactive magnetron sputtering, electron-beam thermal evaporation, chemical vapor deposition, and the like, and any combination thereof.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments herein include:

Embodiment A

An optical computing device comprising: an electromagnetic radiation source to emit electromagnetic radiation into an optical train; an integrated computational element (ICE) located in the optical train before or after a sample located in the optical train to generate modified electromagnetic radiation in the optical train; a broadband angle-selective filter (BASF) located in the optical train to transmit the electromagnetic radiation and/or the modified electromagnetic radiation in the optical train at a target incident angle, thereby generating angle selected-modified electromagnetic radiation (ASMR), and to reflect one or more stray radiation reflections at angles that are not coincident with the target incident angle; and a detector to receive the ASMR and to generate an output signal corresponding to a characteristic of the sample.

Embodiment A may have one or more of the following additional elements in any combination:

Element A1

Wherein the ICE is located after the sample so that the electromagnetic radiation first optically interacts with the sample to generate optically interacted radiation in the optical train, and then the optically interacted radiation optically interacts with the ICE to generate the modified electromagnetic radiation in the optical train, and wherein the BASF is located in the optical train to transit the electromagnetic radiation, the optically interacted radiation, and/or the modified electromagnetic radiation in the optical train at a target incident angle.

Element A2

Wherein the ICE is located before the sample so that the electromagnetic radiation first optically interacts with the ICE to generate optically interacted radiation in the optical train, and then the optically interacted radiation optically interacts with the sample to generate the modified electromagnetic radiation in the optical train, and wherein the BASF is located in the optical train to transit the electromagnetic radiation, the optically interacted radiation, and/or the modified electromagnetic radiation in the optical train at a target incident angle.

Element A3

Wherein the BASF is a stand-alone filter.

Element A4

Wherein BASF is a stand-alone filter arranged in the optical train at a location selected from the group consisting of between the electromagnetic radiation source and the sample, between the sample and the ICE, between the ICE and the detector, and any combination thereof.

Element A5

Wherein the BASF is a multi-layer film stack deposited onto a component selected from the group consisting of the ICE, the detector, and any combination thereof.

Element A6

Wherein a sample window is arranged adjacent to the sample in the optical train, the sampling window having one or more surfaces to generate at least one of the one or more of the stray radiation reflections.

Element A7

Wherein a sample window is arranged adjacent to the sample in the optical train, the sampling window having one or more surfaces to generate at least one of the one or more of the stray radiation reflections, and wherein the BASF is a multi-layer film stack deposited onto a component selected from the group consisting of the ICE, the detector, the sampling window, and any combination thereof.

Element A8

Wherein the BASF is composed of photonic crystal layers.

Element A9

Wherein the BASF is composed of photonic crystal layers selected from the group consisting of a silicon-based compound, a tantalum-based compound, a Group III-V semiconductor compound, a Group IVB metal compound, a dielectric, and any combination thereof.

Element A10

Wherein the electromagnetic radiation source is selected from the group consisting of a light bulb, a light emitting device, a laser, a blackbody, a photonic crystal, an X-Ray source, a gamma ray source, and any combination thereof.

Element A11

Wherein the electromagnetic radiation is at least one selected from the group consisting of infrared radiation, near-infrared radiation, visible light, ultraviolet light, vacuum ultraviolet light, X-ray radiation, gamma ray radiation, and any combination thereof.

By way of non-limiting example, exemplary combinations applicable to A include: A with A1 and A2; A with A1 and A3; A with A1 and A4; A with A1 and A5; A with A1 and A6; A with A1 and A7; A with A1 and A8; A with A1 and A9; A with A1 and A10; A with A1 and A11; A with A2 and A3; A with A2 and A4; A with A2 and A5; A with A2 and A6; A with A2 and A7; A with A2 and A8; A with A2 and A9; A with A2 and A10; A with A2 and A11; A with A3 and A4; A with A3 and A5; A with A3 and A6; A with A3 and A7; A with A3 and A8; A with A3 and A9; A with A3 and A10; A with A3 and A11; A with A4 and A5; A with A4 and A6; A with A4 and A7; A with A4 and A8; A with A4 and A9; A with A4 and A10; A with A4 and A11; A with A5 and A6; A with A5 and A7; A with A5 and A8; A with A5 and A9; A with A5 and A10; A with A5 and A11; A with A6 and A7; A with A6 and A8; A with A6 and A9; A with A6 and A10; A with A6 and A11; A with A7 and A8; A with A7 and A9; A with A8 and A9; A with A8 and A10; A with A8 and A11; A with A9 and A10; A with A9 and A11; A with A10 and A11; A with A1, A2, A3, A4, A5, A6, A7, A8, A9, A10, and A11; A with A1, A3, A5, and A8; A with A1, A2, A6, and A9; A with A5, A7, and A8; A with A1, A2, A10, and A11.

Embodiment B

A method comprising: providing an electromagnetic radiation source that emits electromagnetic radiation into an optical train; optically interacting the electromagnetic radiation with a sample located in the optical train and an integrated computational element (ICE) located in the optical train before or after the sample to generate electromagnetic radiation in the optical train; transmitting the electromagnetic radiation and/or the modified electromagnetic radiation through a broadband angle-selective filter (BASF) located in the optical train at a target incident angle, thereby generating angle-selected modified electromagnetic radiation (ASMR); reflecting one or more stray radiation reflections with the BASF in the optical train at angles that are not coincident with the target incident angle; receiving ASMR with a detector; and generating an output signal corresponding to a characteristic of the sample.

Embodiment B may have one or more of the following additional elements in any combination:

Element B1

Wherein the ICE is located after the sample so that the electromagnetic radiation first optically interacts with the sample to generate optically interacted radiation in the optical train, and then the optically interacted radiation optically interacts with the ICE to generate the modified electromagnetic radiation in the optical train, and wherein the BASF is located in the optical train to transit the electromagnetic radiation, the optically interacted radiation, and/or the modified electromagnetic radiation in the optical train at a target incident angle.

Element B2

Wherein the ICE is located before the sample so that the electromagnetic radiation first optically interacts with the ICE to generate optically interacted radiation in the optical train, and then the optically interacted radiation optically interacts with the sample to generate the modified electromagnetic radiation in the optical train, and wherein the BASF is located in the optical train to transit the electromagnetic radiation, the optically interacted radiation, and/or the modified electromagnetic radiation in the optical train at a target incident angle.

Element B3

Wherein the BASF is a stand-alone filter.

Element B4

Wherein the BASF is a stand-alone filter, and further comprising arranging the BASF stand-alone filter at a location selected from the group consisting of between the electromagnetic radiation source and the sample, between the sample and the ICE, between the ICE and the detector, and any combination thereof.

Element B5

Wherein the BASF is a multi-layer film stack, and further comprising depositing the BASF multi-layer film on a component selected from the group consisting of the ICE, the detector, and any combination thereof.

Element B6

Further comprising arranging a sample window adjacent to the sample and transmitting the electromagnetic radiation therethrough to optically interact with the sample, the sampling window having one or more surfaces that generates at least one of the one or more of the stray radiation reflections.

Element B7

Wherein the BASF is a multi-layer film stack deposited onto a selected from the group consisting of the ICE, the detector, the sampling window, and any combination thereof.

Element B8

Wherein the BASF is composed of photonic crystal layers.

Element B9

Wherein the BASF is composed of photonic crystal layers selected from the group consisting of a silicon-based compound, a tantalum-based compound, a Group III-V semiconductor compound, a Group IVB metal compound, a dielectric, and any combination thereof.

Element B10

Wherein the electromagnetic radiation source is selected from the group consisting of a light bulb, a light emitting device, a laser, a blackbody, a photonic crystal, an X-Ray source, a gamma ray source, and any combination thereof.

Element B11

Wherein the electromagnetic radiation is at least one selected from the group consisting of infrared radiation, near-infrared radiation, visible light, ultraviolet light, vacuum ultraviolet light, X-ray radiation, gamma ray radiation, and any combination thereof.

By way of non-limiting example, exemplary combinations applicable to B include: B with B1 and B2; B with B1 and B3; B with B1 and B4; B with B1 and B5; B with B1 and B6; B with B1 and B7; B with B1 and B8; B with B1 and B9; B with B1 and B10; B with B1 and B11; B with B2 and B3; B with B2 and B4; B with B2 and B5; B with B2 and B6; B with B2 and B7; B with B2 and B8; B with B2 and B9; B with B2 and B10; B with B2 and B11; B with B3 and B4; B with B3 and B5; B with B3 and B6; B with B3 and B7; B with B3 and B8; B with B3 and B9; B with B3 and B10; B with B3 and B11; B with B4 and B5; B with B4 and B6; B with B4 and B7; B with B4 and B8; B with B4 and B9; B with B5 and B6; B with B5 and B7; B with B5 and B8; B with B5 and B9; B with B5 and B10; B with B5 and B11; B with B6 and B7; B with B6 and B8; B with B6 and B9; B with B6 and B10; B with B6 and B11; B with B7 and B8; B with B7 and B9; B with B7 and B10; B with B7 and B11; B with B8 and B9; B with B8 and B10; B with B8 and B11; B with B9 and B10; B with B9 and B11; B with B10 and B11; B with B1, B2, B3, B4, B5, B6, B7, B8, B9, B10, and B11; B with B1, B2, B7, and B9; B with B1, B3, B6, and B8; B with B4, B7, and B9; B with B1, B10, and B11.

Embodiment C

A system comprising: a sample arranged in an optical train; and an optical computing device arranged in the optical train to optically interact with the sample, the optical computing device comprising: an electromagnetic radiation source to emit electromagnetic radiation into the optical train; an integrated computational element (ICE) located in the optical train before or after the sample located in the optical train to generate modified electromagnetic radiation in the optical train; a broadband angle-selective filter (BASF) located in the optical train to transmit the electromagnetic radiation and/or the modified electromagnetic radiation in the optical train at a target incident angle, thereby generating angle selected-modified electromagnetic radiation (ASMR), and to reflect one or more stray radiation reflections at angles that are not coincident with the target incident angle; and a detector to receive the ASMR and to generate an output signal corresponding to a characteristic of the sample.

Embodiment C may have one or more of the following additional elements in any combination:

Element C1

Wherein the ICE is located after the sample so that the electromagnetic radiation first optically interacts with the sample to generate optically interacted radiation in the optical train, and then the optically interacted radiation optically interacts with the ICE to generate the modified electromagnetic radiation in the optical train, and wherein the BASF is located in the optical train to transit the electromagnetic radiation, the optically interacted radiation, and/or the modified electromagnetic radiation in the optical train at a target incident angle.

Element C2

Wherein the ICE is located before the sample so that the electromagnetic radiation first optically interacts with the ICE to generate optically interacted radiation in the optical train, and then the optically interacted radiation optically interacts with the sample to generate the modified electromagnetic radiation in the optical train, and wherein the BASF is located in the optical train to transit the electromagnetic radiation, the optically interacted radiation, and/or the modified electromagnetic radiation in the optical train at a target incident angle.

Element C3

Wherein sample is in a flow path.

Element C4

Wherein sample is in a flow path located in a wellbore in a subterranean formation.

Element C5

Wherein the BASF is a stand-alone filter.

Element C6

Wherein BASF is a stand-alone filter arranged in the optical train at a location selected from the group consisting of between the electromagnetic radiation source and the sample, between the sample and the ICE, between the ICE and the detector, and any combination thereof.

Element C7

Wherein the BASF is a multi-layer film stack deposited onto a component selected from the group consisting of the ICE, the detector, and any combination thereof.

Element C8

Wherein a sample window is arranged adjacent to the sample in the optical train, the sampling window having one or more surfaces to generate at least one of the one or more of the stray radiation reflections.

Element C9

Wherein a sample window is arranged adjacent to the sample in the optical train, the sampling window having one or more surfaces to generate at least one of the one or more of the stray radiation reflections, and wherein the BASF is a multi-layer film stack deposited onto a component selected from the group consisting of the ICE, the detector, the sampling window, and any combination thereof.

Element C10

Wherein the BASF is composed of photonic crystal layers.

Element C11

Wherein the BASF is composed of photonic crystal layers selected from the group consisting of a silicon-based compound, a tantalum-based compound, a Group III-V semiconductor compound, a Group IVB metal compound, a dielectric, and any combination thereof.

Element C12

Wherein the electromagnetic radiation source is selected from the group consisting of a light bulb, a light emitting device, a laser, a blackbody, a photonic crystal, an X-Ray source, a gamma ray source, and any combination thereof.

Element C13

Wherein the electromagnetic radiation is at least one selected from the group consisting of infrared radiation, near-infrared radiation, visible light, ultraviolet light, vacuum ultraviolet light, X-ray radiation, gamma ray radiation, and any combination thereof.

By way of non-limiting example, exemplary combinations applicable to C include: C with C1 and C2; C with C1 and C3; C with C1 and C4; C with C1 and C5; C with C1 and C6; C with C1 and C7; C with C1 and C8; C with C1 and C9; C with C1 and C10; C with C1 and C11; C with C1 and C12; C with C1 and C13; C with C2 and C3; C with C2 and C4; C with C2 and C5; C with C2 and C6; C with C2 and C7; C with C2 and C8; C with C2 and C9; C with C2 and C10; C with C2 and C11; C with C2 and C12; C with C2 and C13; C with C3 and C4; C with C3 and C5; C with C3 and C6; C with C3 and C7; C with C3 and C8; C with C3 and C9; C with C3 and C10; C with C3 and C11; C with C3 and C12; C with C3 and C13; C with C4 and C5; C with C4 and C6; C with C4 and C7; C with C4 and C8; C with C4 and C9; C with C4 and C10; C with C4 and C11; C with C4 and C12; C with C4 and C13; C with C5 and C6; C with C5 and C7; C with C5 and C8; C with C5 and C9; C with C5 and C10; C with C5 and C11; C with C5 and C12; C with C5 and C13; C with C6 and C7; C with C6 and C8; C with C6 and C9; C with C6 and C10; C with C6 and C11; C with C6 and C12; C with C6 and C13; C with C7 and C8; C with C7 and C9; C with C7 and C10; C with C7 and C11; C with C7 and C12; C with C7 and C13; C with C8 and C9; C with C8 and C10; C with C8 and C11; C with C8 and C12; C with C8 and C13; C with C9 and C10; C with C9 and C11; C with C9 and C12; C with C9 and C13; C with C10 and C11; C with C10 and C12; C with C10 and C13; C with C11 and C12; C with C11 and C13; C with C12 and C13; C with C1, C2, C3, C4, C5, C6, C7, C8, C9, C10, C11, C12, and C13; C with C1, C3, C7, and C8; C with C1, C4, C6, and C9; C with C5, C7, and C8; C with C1, C4, and C10; C with C7, C8, and C11; C with C1, C5, C12, and C13.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. An optical computing device comprising:
an electromagnetic radiation source to emit electromagnetic radiation into an optical train;
an integrated computational element (ICE) located in the optical train to generate modified electromagnetic radiation in the optical train based on the emitted electromagnetic radiation from the electromagnetic radiation source;
a first broadband angle-selective filter (BASF) located before the ICE at a first location in the optical train and a second BASF located after the ICE at a second location in the optical train, the first BASF being configured to receive the electromagnetic radiation to transmit first angle-selected modified electromagnetic radiation (ASMR) using the electromagnetic radiation that is transmitted through the first BASF at a first target incident angle selected for the first location and to reflect one or more stray radiation reflections received at the first BASF at angles that are not coincident with the first target incident angle, the second BASF being configured to receive the modified electromagnetic radiation to transmit second ASMR using the modified electromagnetic radiation that is transmitted through the second BASF at a second target incident angle selected for the second location and to reflect one or more stray radiation reflections received at the second BASF at angles that are not coincident with the second target incident angle; and
a detector to receive at least one of the first ASMR or the second ASMR and to generate an output signal corresponding to a characteristic of a sample.

2. The optical computing device of claim 1, wherein the ICE is either (A) located after the sample so that the electromagnetic radiation first optically interacts with the sample to generate optically interacted radiation in the optical train, and then the optically interacted radiation optically interacts with the ICE to generate the modified electromagnetic radiation in the optical train or (B) located before the sample so that the electromagnetic radiation first optically interacts with the ICE to generate optically interacted radiation in the optical train, and then the optically interacted radiation optically interacts with the sample to generate the modified electromagnetic radiation in the optical train, and
wherein the first BASF receives the electromagnetic radiation when the first location is located before the sample and the ICE or receives the optically interacted radiation when the first location is located between the sample and the ICE.

3. The optical computing device of claim 2, wherein at least one of the first BASF or the second BASF is a multi-layer film stack deposited onto a component selected from the group consisting of the ICE, the detector, and any combination thereof.

4. The optical computing device of claim 2, wherein a sample window is arranged adjacent to the sample in the optical train, the sampling window having one or more surfaces to generate at least one of the one or more of the stray radiation reflections.

5. The optical computing device of claim 4, wherein at least one of the first BASF or the second BASF is a multi-layer film stack deposited onto a component selected from the group consisting of the ICE, the detector, the sampling window, and any combination thereof.

6. The optical computing device of claim 2, wherein the electromagnetic radiation source is selected from the group consisting of a light bulb, a light emitting device, a laser, a blackbody, a photonic crystal, an X-Ray source, a gamma ray source, and any combination thereof.

7. The optical computing device of claim 2, wherein the electromagnetic radiation is at least one selected from the group consisting of infrared radiation, near-infrared radiation, visible light, ultraviolet light, vacuum ultraviolet light, X-ray radiation, gamma ray radiation, and any combination thereof.

8. The optical computing device of claim 1, wherein each of the first BASF and the second BASF is composed of photonic crystal layers, and wherein the photonic crystal layers are selected from the group consisting of a silicon-based compound, a tantalum-based compound, a Group III-V semiconductor compound, a Group IVB metal compound, a dielectric, and any combination thereof.

9. A method comprising:
providing an electromagnetic radiation source that emits electromagnetic radiation into an optical train;
optically interacting the electromagnetic radiation with a sample located in the optical train and an integrated computational element (ICE) located in the optical train to generate modified electromagnetic radiation in the optical train;
transmitting the electromagnetic radiation through a first broadband angle-selective filter (BASF) located before the ICE at a first location in the optical train at a first target incident angle selected for the first location, thereby generating first angle-selected modified electromagnetic radiation (ASMR);
transmitting the electromagnetic radiation through a second BASF located after the ICE at a second location in the optical train at a second target incident angle selected for the second location, thereby generating second ASMR;
reflecting one or more stray radiation reflections received at the first BASF and the second BASF at angles that are not coincident with the first target incident angle and the second target incident angle, respectively;
receiving at least one of the first ASMR or the second ASMR with a detector; and
generating an output signal corresponding to a characteristic of the sample based on the at least one of the received first ASMR or received second ASMR.

10. The method of claim 9, wherein the ICE is either (A) located after the sample so that the electromagnetic radiation first optically interacts with the sample to generate optically interacted radiation in the optical train, and then the optically interacted radiation optically interacts with the ICE to generate the modified electromagnetic radiation in the optical train or (B) located before the sample so that the electromagnetic radiation first optically interacts with the ICE to generate optically interacted radiation in the optical train, and then the optically interacted radiation optically interacts with the sample to generate the modified electromagnetic radiation in the optical train, and
wherein the first BASF receives the electromagnetic radiation when the first location is located before the sample and the ICE or receives the optically interacted radiation when the first location is located between the sample and the ICE.

11. The method of claim 10, wherein at least one of the first BASF or the second BASF is a multi-layer film stack, and further comprising depositing the BASF multi-layer film on a component selected from the group consisting of the ICE, the detector, and any combination thereof.

12. The method of claim 10, further comprising arranging a sample window adjacent to the sample and transmitting the electromagnetic radiation therethrough to optically interact with the sample, the sampling window having one or more surfaces that generates at least one of the one or more of the stray radiation reflections.

13. The method of claim 12, wherein at least one of the first BASF or the second BASF is a multi-layer film stack deposited onto a selected from the group consisting of the ICE, the detector, the sampling window, and any combination thereof.

14. The method of claim 9, wherein each of the first BASF and the second BASF is composed of photonic crystal layers, and wherein the photonic crystal layers are selected from the group consisting of a silicon-based compound, a tantalum-based compound, a Group III-V semiconductor compound, a Group IVB metal compound, a dielectric, and any combination thereof.

15. A system comprising:
a sample arranged in an optical train; and
an optical computing device arranged in the optical train to optically interact with the sample, the optical computing device comprising:
an electromagnetic radiation source to emit electromagnetic radiation into the optical train;
an integrated computational element (ICE) located in the optical train to generate modified electromagnetic radiation in the optical train based on the emitted electromagnetic radiation from the electromagnetic radiation source;
a first broadband angle-selective filter (BASF) located before the ICE at a first location in the optical train and a second BASF located after the ICE at a second location in the optical train, the first BASF being configured to receive the electromagnetic radiation to transmit first angle-selected modified electromagnetic radiation (ASMR) using the electromagnetic radiation that is transmitted through the first BASF at a first target incident angle selected for the first location and to reflect one or more stray radiation reflections received at the first BASF at angles that are not coincident with the first target incident angle, the second BASF being configured to receive the modified electromagnetic radiation to transmit second ASMR using the modified electromagnetic radiation that is transmitted through the second BASF at a second target incident angle selected for the second location and to reflect one or more stray radiation reflections received at the second BASF at angles that are not coincident with the second target incident angle; and
a detector to receive at least one of the first ASMR or the second ASMR and to generate an output signal corresponding to a characteristic of the sample.

16. The system of claim 15, wherein the ICE is either (A) located after the sample so that the electromagnetic radiation first optically interacts with the sample to generate optically interacted radiation in the optical train, and then the optically interacted radiation optically interacts with the ICE to generate the modified electromagnetic radiation in the optical train or (B) located before the sample so that the electromagnetic radiation first optically interacts with the ICE to generate optically interacted radiation in the optical train, and then the optically interacted radiation optically interacts with the sample to generate the modified electromagnetic radiation in the optical train, and
wherein the first BASF receives the electromagnetic radiation when the first location is located before the sample and the ICE or receives the optically interacted radiation when the first location is located between the sample and the ICE.

17. The system of claim 16, wherein sample is in a flow path.

18. The system of claim 17, wherein the flow path is located in a wellbore in a subterranean formation.

* * * * *